US006348475B1

(12) United States Patent
Zhang et al.

(10) Patent No.: US 6,348,475 B1
(45) Date of Patent: Feb. 19, 2002

(54) METHODS, COMPOUNDS AND COMPOSITIONS FOR TREATING GOUT

(75) Inventors: Jie Zhang, Ellicott City; Jia-He Li, Cockeysville, both of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/870,782

(22) Filed: Jun. 1, 2001

Related U.S. Application Data

(60) Provisional application No. 60/208,328, filed on Jun. 1, 2000.

(51) Int. Cl.$^7$ .................. A61K 31/165; A61K 31/47
(52) U.S. Cl. .................. 514/309; 514/617; 514/619
(58) Field of Search ................ 514/309, 617, 514/619

(56) References Cited

U.S. PATENT DOCUMENTS

| | | |
|---|---|---|
| 932,290 A | 8/1909 | Kacer et al. |
| 1,001,325 A | 8/1911 | Ullman et al. |
| 1,253,252 A | 1/1918 | Kardos et al. |
| 1,880,441 A | 10/1932 | Heidenreich et al. |
| 1,895,105 A | 1/1933 | Rath et al. |
| 2,467,692 A | 4/1949 | Petrow et al. |
| 2,593,798 A | 4/1952 | Robinson |
| 2,612,503 A | 9/1952 | Ullyot |
| 2,638,472 A | 5/1953 | Grewe |
| 2,666,059 A | 1/1954 | Davis et al. |
| 2,700,040 A | 1/1955 | Ullyot |
| 2,892,841 A | 6/1959 | Rudner |
| 2,992,220 A | 7/1961 | Irving et al. |
| 3,247,212 A | 4/1966 | Johnson |
| 3,291,801 A | 12/1966 | Montgomery |
| 3,300,499 A | 1/1967 | Lesher et al. |
| 3,403,157 A | 9/1968 | Humber et al. |
| 3,507,872 A | 4/1970 | Hegar |
| 3,534,038 A | 10/1970 | Machatzke et al. |
| 3,557,119 A | 1/1971 | Humber et al. |
| 3,573,304 A | 3/1971 | Eberle et al. |
| 3,700,673 A | 10/1972 | Watson, Jr. |
| 3,719,684 A | 3/1973 | Unger et al. |
| 3,723,436 A | 3/1973 | Hollstein et al. |
| 3,759,924 A | 9/1973 | Jeanmart et al. |
| 3,830,816 A | 8/1974 | Gittos et al. |
| 3,838,134 A | 9/1974 | Glauthier |
| 3,899,529 A | 8/1975 | Witzel |
| 3,900,477 A | 8/1975 | Philipp et al. |
| 3,904,671 A | 9/1975 | Minatoya |
| 3,932,643 A | 1/1976 | Gauthier |
| 3,950,343 A | 4/1976 | Philipp et al. |
| 3,978,066 A | 8/1976 | Philipp et al. |
| 3,991,064 A | 11/1976 | Brown et al. |
| 4,031,097 A | 6/1977 | Bach et al. |
| 4,082,741 A | 4/1978 | Hunger et al. |
| 4,169,897 A | 10/1979 | Meyer et al. |

(List continued on next page.)

FOREIGN PATENT DOCUMENTS

| | | |
|---|---|---|
| BE | 562948 | 4/1960 |
| BE | 628255 | 2/1963 |
| CA | 1000701 | 11/1976 |
| CA | 1274339 | 9/1990 |
| CA | 1278141 | 12/1990 |
| CH | 463 778 | 10/1968 |
| DE | 282711 | 3/1915 |
| DE | 963 184 | 5/1957 |
| DE | 2111910 | 10/1971 |
| DE | 2429515 | 6/1973 |
| DE | 26 50 226 | 5/1978 |
| DE | 33 32 633 A | 4/1985 |
| EP | 0 005 232 A | 6/1982 |
| EP | 0 126 684 B1 | 11/1984 |
| EP | 0 212 959 B1 | 3/1986 |
| EP | 0 197 718 B1 | 10/1986 |
| EP | 355 750 | 2/1990 |
| EP | 0 555 750 | 2/1990 |
| EP | 393926 | 10/1990 |
| EP | 0 393 926 | 10/1990 |

(List continued on next page.)

OTHER PUBLICATIONS

WO for PCT/US99/30971 PCT/US99/30971 2000.
Abstr Pap Am Chem Soc. 206 (2) 1993 Slama et al.
Abstract 1994:425593 1994 Zailsev et al.
Aldrich Catalog #23,559–8.
Angew. Chem. 76:1,50 1964 Baer et al.
Ann. 673:132–36 1964 Reid et al.
Ann. Chem. 688:177–188 1965 Reid et al.
Ann. N Y Acad Sci. 825:366–379 1997 Cosi et al.
Annu. Rev. Neurosci 13, 171–182 1990 Choi et al.
Anticancer Drug Des. 7:107–117 1991 Suto et al.
Anticancer Drug Design 10(6)507–514 (Sep.) 1995 Griffin et al.
Anticancer Research 11:881–888 1991 Sakagami et al.
Arch. Pharm. Ber. Dtsch. Pharm. Ges. 300:6, 533–539 1967 Reisch.
Beilstein Handbook of Organic Chem. Reg. No. 158523 1950.
Beilstein Handbook of Organic Chem. Reg. No. 233692 1956.
Beilstein Handbook of Organic Chem. Reg. No. 618403 1988 Dokunichin.
Beilstein Handbook of Organic Chem. Reg. No. 827161 1988 Dokunichin.
Beilstein Handbook of Organic Chem. Reg. No. 821484 1988 Dokunichin.
Beilstein Handbook of Organic Chem. Reg. No. 619108 1988 Dokunichin.

(List continued on next page.)

*Primary Examiner*—Raymond Henley, III
(74) *Attorney, Agent, or Firm*—Nixon & Vanderhye P.C.

(57) ABSTRACT

This invention relates to methods of preventing, treating or lessening the severity of gout by administration of PARP inhibitors.

4 Claims, No Drawings

U.S. PATENT DOCUMENTS

| | | | |
|---|---|---|---|
| 4,218,453 A | 8/1980 | Hannart | |
| 4,309,543 A | 1/1982 | Keeley | |
| 4,382,943 A | 5/1983 | Winter et al. | |
| RE31,617 E | 6/1984 | Beverung, Jr. et al. | |
| 4,472,401 A | 9/1984 | Kennewell et al. | |
| 4,594,415 A | 6/1986 | Robins et al. | |
| 4,639,454 A | 1/1987 | Hesson | |
| 4,740,581 A | 4/1988 | Pruett et al. | |
| 4,742,171 A | 5/1988 | Martin et al. | |
| 4,902,695 A | 2/1990 | Ornstein | |
| 4,902,798 A | 2/1990 | Nakamatsu et al. | |
| 4,925,968 A | 5/1990 | Sestanj et al. | |
| 5,032,617 A | 7/1991 | Lee et al. | |
| 5,041,653 A | 8/1991 | Lee et al. | |
| 5,077,035 A | 12/1991 | Wieland et al. | |
| 5,177,075 A * | 1/1993 | Suto et al. | 514/248 |
| 5,215,738 A | 6/1993 | Lee et al. | |
| 5,262,564 A | 11/1993 | Schohe et al. | |
| 5,274,097 A | 12/1993 | Schohe et al. | |
| 5,338,851 A | 8/1994 | Huff et al. | |
| 5,391,376 A | 2/1995 | Long, Jr. et al. | |
| 5,391,554 A * | 2/1995 | Showalter | 514/300 |
| 5,395,835 A | 3/1995 | Glase et al. | |
| 5,414,001 A | 5/1995 | Ireland et al. | |
| 5,420,136 A | 5/1995 | Lewis et al. | |
| 5,434,188 A | 7/1995 | Boschelli et al. | |
| 5,464,871 A | 11/1995 | Kun et al. | |
| 5,473,074 A | 12/1995 | Kun et al. | |
| 5,480,631 A | 1/1996 | De Paulis et al. | |
| 5,482,975 A | 1/1996 | Kun et al. | |
| 5,516,941 A | 5/1996 | Kun et al. | |
| 5,587,384 A * | 12/1996 | Zhang et al. | 514/309 |
| 5,589,483 A | 12/1996 | West | |
| 5,618,813 A | 4/1997 | Chu et al. | |
| 5,633,282 A | 5/1997 | Collins et al. | |
| 5,635,506 A | 6/1997 | Alberts et al. | |
| 5,652,260 A | 7/1997 | Kun et al. | |
| 5,652,367 A | 7/1997 | Kun et al. | |
| 5,656,638 A | 8/1997 | Gaeta et al. | |
| 5,659,082 A | 8/1997 | Flitter et al. | |
| 5,665,710 A | 9/1997 | Rahman et al. | |
| 5,670,518 A | 9/1997 | Kun et al. | |
| 5,703,089 A | 12/1997 | Braña et al. | |
| 5,703,116 A | 12/1997 | Gaeta et al. | |
| 5,719,151 A | 2/1998 | Shall et al. | |
| 5,753,674 A | 5/1998 | Kun et al. | |
| 5,756,510 A | 5/1998 | Griffin et al. | |
| 5,760,062 A | 6/1998 | Gaeta et al. | |
| 5,767,135 A | 6/1998 | Fernandez-Pol | |
| RE36,397 E | 11/1999 | Zhang et al. | |
| 6,121,278 A | 9/2000 | Jackson et al. | |
| 6,197,785 B1 | 3/2001 | Jackson et al. | |
| 6,201,020 B1 | 3/2001 | Zhang | |
| 6,235,748 B1 | 5/2001 | Li et al. | |

FOREIGN PATENT DOCUMENTS

| | | |
|---|---|---|
| EP | 0 219 208 B1 | 6/1992 |
| EP | 0 539 508 | 5/1993 |
| EP | 0 638 309 A1 | 2/1995 |
| EP | 0676 201 | 10/1995 |
| FR | 1 199 252 | 12/1957 |
| FR | 7 723 M | 11/1971 |
| FR | 2 205 333 | 7/1974 |
| FR | 2 305 182 | 11/1976 |
| GB | 810108 | 3/1959 |
| GB | 838994 | 6/1960 |
| GB | 1263044 | 2/1972 |
| GB | 1379111 | 1/1975 |
| GB | 1474775 | 5/1977 |
| GB | 1545767 | 5/1979 |
| JP | 032 05402 A2 | 9/1991 |
| JP | 3-205402 | 9/1991 |
| JP | 040 13684 A2 | 1/1992 |
| JP | 4-13684 | 3/1992 |
| JP | 4-275223 | 9/1992 |
| JP | 042 75223 A2 | 9/1992 |
| JP | 042 75296 A2 | 9/1992 |
| JP | 4-275296 | 9/1992 |
| WO | WO 90/07502 | 7/1990 |
| WO | WO 92/00281 | 1/1992 |
| WO | WO 92/05770 | 4/1992 |
| WO | WO 92/15286 | 9/1992 |
| WO | WO 93/05096 | 3/1993 |
| WO | WO 93/18748 | 9/1993 |
| WO | WO 95/04720 | 2/1995 |
| WO | WO 95/24379 | 9/1995 |
| WO | WO 95/29895 | 11/1995 |
| WO | WO 95/30409 | 11/1995 |
| WO | WO 96/28167 | 9/1996 |
| WO | WO 96/33268 | 10/1996 |
| WO | WO 97/30054 | 8/1997 |
| WO | WO 97/38977 | 10/1997 |
| WO | WO 98/27975 | 7/1998 |
| WO | WO 99/11622 | 3/1999 |
| WO | WO 99/11623 | 3/1999 |
| WO | WO 99/11624 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |
| WO | WO 00/39070 | 7/2000 |
| WO | WO 00/39104 | 7/2000 |
| WO | WO 01/16137 | 3/2001 |

OTHER PUBLICATIONS

Beilstein Handbook of Organic Chem. Reg. No. 657772 1988 Dokunichin.

Beilstein Handbook of Organic Chem. Reg. No. 6538881988 Dokunichin.

Beilstein Handbook of Organic Chem. Reg. No. 807993 1988 Sielitz.

Beilstein Handbook of Organic Chem. Reg. No. 746893 1988 Dokunichin.

Beilstein Handbook of Organic Chem. Reg. No. 656117 1988 Gomes.

Beilstein Handbook of Organic Chem. Reg. No. 1571164 1988 Rokach.

Beilstein Handbook of Organic Chem. Reg. No. 1541605 1988 Humber et al.

Beilstein Handbook of Organic Chem. Reg. No. 751834 1988 Mavoungou Gomes.

Beilstein Handbook of Organic Chem. Reg. No. 670954 1988 Mavoungou Gomes.

Beilstein Handbook of Organic Chem. Reg. No. 649696 1988 Dokunikhin.

Beilstein Handbook of Organic Chem. Reg. No. 530731 1988 Dokunichin.

Beilstein Handbook of Organic Chem. Reg. No. 660681 1988 Dokunichin.

Beilstein Handbook of Organic Chem. Reg. No. 4483194 1991 Oleinik.

Beilstein Handbook of Organic Chem. Reg. No. 4494786 1991 Oleinik.

Beilstein Handbook of Organic Chem. Reg. No. 3140506 1998.

Beilstein Handbook of Organic Chem. Reg. No. 56052 1998.
Beilstein Handbook of Organic Chem. Reg. No. 332938 1998.
Beilstein Handbook of Organic Chem. Reg. No. 254129 1998.
Beilstein Handbook of Organic Chem. Reg. No. 245245 1998.
Beilstein Handbook of Organic Chem. Reg. No. 244756 1998.
Beilstein Handbook of Organic Chem. Reg. No. 222316 1998.
Beilstein Handbook of Organic Chem. Reg. No. 207532 1998.
Beilstein Handbook of Organic Chem. Reg. No. 207516 1998.
Beilstein Handbook of Organic Chem. Reg. No. 165349 1998.
Beilstein Handbook of Organic Chem. Reg. No. 161148 1998.
Beilstein Handbook of Organic Chem. Reg. No. 2213597 1999.
Beilstein Handbook of Organic Chem. Reg. No. 13823 1999.
Biochem. J. 185, 775–777 1980 Purnell et al.
Biochemical and Biophysical Research 136(3), 1110–1115 1986 Tanuma et al.
Biochemical and Biophysical Research Communications 195, No. 2, 558–564 1993 Jesser et al.
Biochemical and Biophysical Research Communications 195(2), 558–564 1993 Jesser et al.
Biochemical and Biophysical Research Communications 210, No. 2, 329–337 1995 Aoki et al.
Biochemical and Biophysical Research Communications 220, 411–417 1996 Uchiumi et al.
Biochemical and Biophysical Research Communications 236, 265–269 1997 Maruta et al.
Biochemical and Biophysical Research Communications 245,1–10 1998 Rhun et al.
Biochemical and Biophysical Research Communications 278(3) Nov. 30, 2000, 590–598 2000 Zhang et al.
Biochemical Society Transactions vol. 8(2), 192–193 1980 Whitby et al.
Biochemical Society Transactions 21:330–334 1993 Beckman et al.
Biochemistry 30, 5907–5912 1991 Maruta et al.
Biochemistry International 16, No. 3, 397–403 1988 Concha et al.
Biochemistry International 19, No. 6, 1395–1402 1989 Tanuma et al.
Biochemistry International 18, No. 4, 701–708 1989 Tanuma et al.
Biochemistry International 24, No. 5, 889–897 1991 Tsai et al.
Biochimica et Biophysica Acta 827, 228–234 1985 Tavassoli et al.
Biochimica et Biophysica Actas 1158, 251–256 1993 Aoki et al.
Biochimie vol. 77 No. 6, pp. 408–422 1995 Griffin et al.
Br. J. Pharm. 117:619–632 1996 Southan et al.
Brain Res. 710:169–177 1996 Wallis et al.
Brain Res. 729:264–269 1996 Cosi et al.
Brain Research 809:58–67 1998 Cosi et al.
Brain 122, 247–253 1999 Love et al.
Brit. J. Pharm. 122:493–503 1997 Cuzzocrea.
Bull. Chem. Soc. Jpn. 61(6):2238–2240 1988 Sato et al.
Bull. Soc. Chim. Fr. 233 1962 Granger et al.
C. R. Acad. Sci. 275:17, 961–964 1972 Michailidis et al.
Can J. Chem. 73, 319–335 1995 Desilets et al.
Can. J. Chem. vol. 49, 2797–2802 1971 Horning.
Cell 94, 325–337 1998 Kuida et al.
Cell 94, 339–352 1998 Hakem et al.
Cell Biology and Toxicology 9, No. 2, 165–175 1993 Clayson et al.
Cerebrovascular Disease 319–325 1997 Dawson et al.
Chem Abstracts 52:17 (14606h) (Sep. 10) 1958 Ochiai et al.
Chem Abstracts 55:6 (5491ce) (Mar. 20) 1961 Ochiai et al.
Chem Abstracts 58:4 (3425d) (Feb. 18) 1963 Hayashi et al.
Chem Abstracts vol. 126,No. 17,229493f Apr. 28, 1997 Angeliki.
Chem. Abstracts 64:695e 1966 Reid et al.
Chem. Ber. 46, pp. 2087–2089 1913 Kardos.
Chemical Abstract 54:22648a 1995 Nikitskaya et al.
Chemical Abstract vol. 51:1960 1957 Taylor et al.
Chemical Abstract vol. 52:5846a 1958 Schmidt–Nickels.
Chemical Abstract vol. 52:6285 1958 Ohta.
Chemical Abstract vol. 52:4646 1958 Gilman et al.
Chemical Abstract vol. 52:5846b 1958 Gateff et al.
Chemical Abstract vol. 54:22647 1960 Campbell.
Chemical Abstract vol. 55:12868a 1961.
Chemical Abstract vol. 55:12868b 1961.
Chemical Abstract vol. 55:12868c 1961.
Chemical Abstract vol. 58:7884 1963 Sieglitz.
Chemical Abstract vol. 59:10037b 1963 Dokunikhin et al.
Chemical Abstract vol. 59:10037c 1963 Hazard et al.
Chemical Abstract vol. 61:15194 1964 Tsuboi.
Chemical Abstract vol. 61:13305h 1964 Quelet.
Chemical Abstract vol. 61:9493g 1964 Dokunikhin et al.
Chemical Abstract vol. 61:9494a 1964 Dokunikhin et al.
Chemical Abstract vol. 61:9493f 1964 Bodea et al.
Chemical Abstract vol. 61:13305g 1964 Badger et al.
Chemical Abstract vol. 63:7006 1965 Perrin.
Chemical Abstract vol. 62:5259 1965 Lakeside Lab., Inc.
Chemical Abstract vol. 62:9129e 1965 Kuehn.
Chemical Abstract vol. 63:4256 1965 Keene et al.
Chemical Abstract vol. 62:9129g 1965 Klosa.
Chemical Abstract vol. 65:15320a 1966 Kametani.
Chemical Abstract vol. 64:3526h 1966 Crossland.
Chemical Abstract vol. 65:15319h 1966 Humber et al.
Chemical Abstract vol. 69:87767 1968 Hofer.
Chemical Abstract vol. 68:59420 1968 Chandler et al.
Chemical Abstract vol. 70:3629 1969 Weis.
Chemical Abstract vol. 70:67988 1969 Resplandy et al.
Chemical Abstract vol. 70:115926 1969 Hofer.
Chemical Abstract vol. 70:4079 1969 Coyne et al.
Chemical Abstract vol. 73:35200 1970 Pan et al.
Chemical Abstract vol. 72:121337 1970 Pan et al.
Chemical Abstract vol. 74:111797 1971 Mavoungou–Gomes.
Chemical Abstract vol. 75:98422 1971 Campbell.
Chemical Abstract 74:110112y (p. 252 May 10) 1971 Damas.
Chemical Abstract vol. 77:61927 1972 Zinchenko.
Chemical Abstract vol. 76:14566 1972 Rodway.
Chemical Abstract vol. 76:85774 1972 Mavoungou–Gomes.
Chemical Abstract vol. 78:123624 1973 Swenton et al.
Chemical Abstract vol. 78:68700 1973 Roehm et al.
Chemical Abstract vol. 78:58193 1973 Mondon et al.

Chemical Abstract vol. 78:84227 1973 Kraatz et al.
Chemical Abstract vol. 78:29384 1973 Forrester et al.
Chemical Abstract vol. 78:29593 1973 Cerbai et al.
Chemical Abstract vol. 81:37489 1974 Cerbai et al.
Chemical Abstract vol. 81:37417 1974 Baddar.
Chemical Abstract vol. 81:171011 1975 Rodway.
Chemical Abstract vol. 82:170471 1975 Mavoungou–Gomes.
Chemical Abstract vol. 83:27978 1975 Baddar.
Chemical Abstract vol. 84:42754 1976 Zaitsev.
Chemical Abstract vol. 84:3986 1976 Zaitsev.
Chemical Abstract vol. 85:182 1976 Tullar et al.
Chemical Abstract vol. 84:16943 1976 Minatoya et al.
Chemical Abstract vol. 85:77216 1976 Ege et al.
Chemical Abstract vol. 84:4857 1976 Cookson.
Chemical Abstract 85(1976)159898a 1976.
Chemical Abstract vol. 86:171282 1977 Humber.
Chemical Abstract vol. 87:152015 1977 Houlihan.
Chemical Abstract vol. 87:5778 1977 Fomenko et al.
Chemical Abstract vol. 82:30602 1978 Minatoya et al.
Chemical Abstract vol. 90:6486t 1979 Takahashi.
Chemical Abstract vol. 91:39035 1979 Migachev.
Chemical Abstract vol. 90:38734 1979 Mavoungou–Gomes.
Chemical Abstract vol. 92:181104e 1980 Ryabukhina et al.
Chemical Abstract vol. 92:146482 1980 Rokach.
Chemical Abstract vol. 92:41620 1980 Migachev et al.
Chemical Abstract vol. 92:41511 1980 Migachev et al.
Chemical Abstract vol. 93:26178 1980 Gomes.
Chemical Abstract vol. 92:198336 1980 Cabares.
Chemical Abstract 92:22393 1980 Simmonds.
Chemical Abstract vol. 95:80661 1981 Narasimhan et al.
Chemical Abstract vol. 95 (9):80666 1981 Migachev et al.
Chemical Abstract vol. 95:80688 1981 Migachev et al.
Chemical Abstract vol. 95:42867 1981 Migachev et al.
Chemical Abstract vol. 95:42866 1981 Migachev et al.
Chemical Abstract vol. 95:187120 1981 Migachev et al.
Chemical Abstract vol. 95:168911 1981 Houlihan.
Chemical Abstract vol. 96:6539m, p. 592 1982 Singh et al.
Chemical Abstract vol. 96:68519 1982 Leardini et al.
Chemical Abstract vol. 97:38635 1982 Krepelka.
Chemical Abstract vol. 97:126680 1982 Grimshaw et al.
Chemical Abstract vol. 100:103453 1984 Prostakov et al.
Chemical Abstract vol. 100:191713 1984 Orlic–Nuber et al.
Chemical Abstract vol. 100:139054 1984 Oleinik.
Chemical Abstract vol. 102:203854 1985 Migachev et al.
Chemical Abstract vol. 105:60505 1986 Andrievskii et al.
Chemical Abstract vol. 106 (67553) 1987 Pellefier.
Chemical Abstract vol. 107:23262 1987 Cabares.
Chemical Abstract vol. 107:39655v 1987 Bondarenko et al.
Chemical Abstract vol. 108:21627 1988 Duval.
Chemical Abstract vol. 110:230971 1989 Val'kova et al.
Chemical Abstract vol. 113:190649 1990 Val'kova et al.
Chemical Abstract vol. 112:44716 1990 Korol'kova et al.
Chemical Abstract vol. 112:128235 1990 Korol'kova et al.
Chemical Abstract vol. 112:216749 1990 Benson et al.
Chemical Abstract vol. 114:143456 1991 Walser.
Chemical Abstract vol. 115 (232107) 1991 Nagao.
Chemical Abstract vol. 115:70731f 1991 Donshikh et al.
Chemical Abstract vol. 115:158338 1991 Buckman et al.
Chemical Abstract vol. 114:42543 1991 Andrievskii et al.
Chemical Abstract vol. 119:72127 1993 Zaitsev et al.
Chemical Abstract vol. 118:191567 1993 Dow.
Chemical Abstract vol. 118:80722 1993 Dininno et al.
Chemical Abstract vol. 118:101709 1993 Dininno et al.

Chemical Abstract vol. 120:134231 1994 Rocca et al.
Chemical Abstract vol. 121:220651v 1994 Pawlowska et al.
Chemical Abstract vol. 121:172572 1994 Liu et al.
Chemical Abstract vol. 120:95793 1994 Kyota et al.
Chemical Abstract vol. 121:57315 1994 Dow et al.
Chemical Abstract vol. 120:148508p 1994 Barros et al.
Chemical Abstract vol. 123:505 1995 Weltin et al.
Chemical Abstract vol. 122:10865 1995 Lamba et al.
Chemical Abstract vol. 122:170499 1995 Korol'kova et al.
Chemical Abstract vol. 123:256711 1995 Kalindjian et al.
Chemical Abstract vol. 122:170250 1995 Gorio et al.
Chemical Abstract vol. 122:187249 1995 Dininno et al.
Chemical Abstract 122:316902 1995 Desilets et al.
Chemical Abstract 122:316901 1995 Desilets et al.
Chemical Abstracts 122:187526 1995 Langlois et al.
Chemical Abstract vol. 125:87882 1996 Yamaguchi et al.
Chemical Abstract vol. 124:331706 1996 Silverman et al.
Chemical Abstract vol. 124:131261 1996 Richter.
Chemical Abstract vol. 126:115554 1996 Malhotra et al.
Chemical Abstract vol. 125:246943 1996 Korol'kova et al.
Chemical Abstract vol. 125:277462 1996 Ge et al.
Chemical Abstract vol. 124:202047 1996 Fernandez et al.
Chemical Abstract vol. 128:36109 1997 Sakai et al.
Chemical Abstract vol. 127:234258 1997 Reddy et al.
Chemical Abstract vol. 127:81282 1997 Marek et al.
Chemical Abstract vol. 128:34752 1997 Jones et al.
Chemical Abstract vol. 127:80243 1997 Banister et al.
Chemical Abstract abstract No. 17462 1998 Yoshida et al.
Chemical Abstract vol. 129:104224 1998 West.
Chemical Abstract vol. 128:138099 1998 Weltin et al.
Chemical Abstract vol. 130:24816 1998 Park et al.
Chemical Abstract vol. 128:75320 1998 Jones et al.
Chemical Abstract vol. 128:165850 1998 Cookson et al.
Chemical Abstract vol. 129:54301 1998 Albright et al.
Chemical Abstract No. 816103 1998 Albright et al.
Chemical Abstracts vol. 52 (21) 18420d 1958 Tanida.
Chemical Abstracts vol. 62, No. 5, 5271c Mar. 1965.
Chemical Abstracts vol. 76 (25) 153704b 1972 Pozharskii et al.
Chemical Abstracts vol. 88 (7) 49887 1978 Szadowski.
Chemical Abstracts 88, No. 13, 505 (88:89502c) 1978 Dokunikhin et al.
Chemical Abstracts 94, No. 23, 637(192098y) 1981 Migachev.
Chemical Abstracts Registry No. 17 1399–15–8 1998.
Chemical Abstracts Registry No. 14223 8–47–9 1998.
Chemical Abstracts 85:159898a 85, No. 21, 531 1974 Upadysheva et al.
Chem. Lett. 39–42 1990 Chiba et al.
Chemical and Pharmaceutical Bulletin vol. 26, No. 12, pp. 3682–3694 1978 Hamada et al.
Chemische Berichte vol. 102, 1161–1176 1969 Kauffmann et al.
Eur. J. Biochem. vol. 244, pp. 15–20 1997 Van Gool et al.
Eur. J. Med Chem. 29, 925–40 1994 Langlois et al.
Eur. J. Pharm. 204, 339–40 1991 Nowicki et al.
Gazz. Chim. Ital. 91:1345–51 1962 Di Maio et al.
Gazz. Chim. Ital. 91:1124–32 1962 Di Maio et al.
Gazz. Chim. Ital. 94:5, 590–94 1964 Di Maio et al.
Hawleys Chemical Condense Dictionary Sax (Ed) 11th Ed, 1987 p. 898 1987 Hawley's.
Heterocycles 22:2, 237–40 1984 Naito et al.
Int. J. Immunopharmac 17, No. 4, 265–271 1995 Weltin et al.

Int. J. Radiat. Biol. vol. 72 No. 6, pp. 685–692 1997 Weltin et al.
Int. J. Radiat. Biol. Relat. Stud. Phys. Chem. Med. vol. 48 No. 5, pp. 675–690 1985 Harris.
Intl. J. Oncol 8:239–52 1996 Bauer et al.
IPER for PCT/US98/18189.
IS&T's Tenth Int'l Congress on 246–248 1994 Richter et al.
ISR for PCT/US98/18185 PCT/US98/18185 1998.
ISR for PCT/US98/18186 PCT/US98/18186 1999.
ISR for PCT/US98/18187 PCT/US98/18187 1997.
ISR for PCT/US98/18188 PCT/US98/18188 1997.
ISR for PCT/US98/18189 PCT/US98/18189 1997.
ISR for PCT/US98/18195 PCT/US98/18195 1997.
ISR for PCT/US98/18196 PCT/US98/18196 1998.
ISR for PCT/US98/18226 PCT/US98/18226 1997.
ISR for PCT/US99/30971 PCT/US99/30971 1998.
ISR for PCT/US99/30979 PCT/US99/30979 1998.
Itsu Kenkusho Nempo 16:15–23 1971 Ochiai et al.
J Cerebral Flood Flow Metabol. 17(11):1143–51 1997 Endres et al.
J Chem. Soc. 11:1293–97 1978 Davies et al.
J. Am. Chem. Soc. 78:5104–8 1956 Taylor et al.
J. Biol. Chem 270:19, 11176–80 1995 Heller et al.
J. Biol. Chem. 246(20), 6362–64 1972 Miwa et al.
J. Biol. Chem. 261 (32), 14902–11 1986 Hatakeyama et al.
J. Biol. Chem. 262(36), 17641–50 1987 Ikejima et al.
J. Biol. Chem. 263(23), 11037–40 1988 Ikejima et al.
J. Biol. Chem. 267(20), 14436–42 1992 Tsai et al.
J. Biol. Chem. 267:3, 1569–75 1992 Banasik et al.
J. Biol. Chem. 272:9030–36 1997 Szabó et al.
J. Chem. Soc. 12:2231–2241 1971 Barton.
J. Chem. Res., Synop. 8:302 1995 Mueller et al.
J. Chem. Res., Synop. 2:126 1996 Mueller et al.
J. Chem. Soc. pp. 1979–1984 1929 Blount et al.
J. Chem. Soc. 1624–28 1958 Johnson.
J. Chem. Soc. 4295–98 1962 Brown et al.
J. Chem. Soc. 1:14, 1747–51 1974 Ninomiya et al.
J. Chem. Soc. 1:7, 763–70 1974 Bailey et al.
J. Chem. Soc. 812 1956 McConnell et al.
J. Exp Med. vol. 186, No. 7, Oct. 6, 1997, 1041–9 1997 Szabo.
J. Het. Chem vol. 7, pp. 597–605 1970 Pan et al.
J. Heterocycl. Chem. 20:5, 1407–9 1983 Rougeot et al.
J. Immuno. 153:3319–25 1994 Hughes et al.
J. Med. Chem. 38, 389–393 1995 Slama et al.
J. Med. Chem. 38, 4332–4336 1995 Slama et al.
J. Med. Pharm. Chem. 3;1961; 157, 159 1961 Gootjes et al.
J. Neurochem 65:3, 1411–14 1995 Zhang et al.
J. Neurosci. 13:6, 2651–61 1993 Dawson et al.
J. Neurosci. 16:8, 2479–87 1996 Dawson et al.
J. Neuroscience Res. 47:372–383 1997 Ceruti et al.
J. of Biological Chemistry 261(2), 965–69 1986 Tanuma et al.
J. Org Chem. 29:3, 681–85 1964 Masamune et al.
J. Org Chem. 47, 2043–2047 1982 Taylor et al.
J. Org. Chem. vol. 23, pp. 1071–1072 Jul. 1958 Robinson et al.
J. Org. Chem. 29:11, 3180–85 1964 Baer et al.
J. Org. Chem. 43:11, 2190–96 1978 Eisch et al.
J. Phys. Org. Chem 10;7;1997; 499–513 1997 Arnett et al.
J. Urol. vol. 150, pp. 1526–1532 1993 Sklar et al.
JACS 71:937–8 (Mar.) 1949 Wilson et al.
JACS 76:4396–8 (Sep. 5) 1954 Wright.
Japanese J. Pharm. 75, Supp. I:102 1997 Szabó et al.
Japanese J. Pharm. 75, Supp. I:15 1997 Salzman et al.
JCS pp. 4067–4075 1952 Peak et al.
JCS pp. 1294–1304 1956 Albert et al.
JCS pp. 2384–2396 1959 Albert et al.
Journal of Cellular Biochemistry 29:361–372 1985 Bolander, Jr.
Journal of Cerebral Blood Flow and Metabolism 17 No. 11, 1137–1142 1997 Takahashi et al.
Journal of Heterocyclic Chemistry vol. 3, pp. 466–469 Dec. 1966 Aparajithan.
Journal of Heterocyclic Chemistry vol. 15, pp. 1513–1514 1978 Nuvole et al.
Journal of Medicinal Chemistry vol. 20 (3) 449–452 1977 Diana et al.
Journal of Medicinal Chemistry 35(5)823–832 1992 Ocain.
Journal of Neurochemistry 70, No. 2, 501–508 1998 Cookson et al.
Journal of Organic Chemistry vol. 11, No. 3, 239–246 1946 Bergstrom et al.
Journal of Organic Chemistry 53(20)4650–3 1988 D. Dumas.
Journal of the Chemical Society pp. 1799–1803 1972 Singh et al.
Journal of the Chemical Society vol. 9, 944–950 1976 Loewenthal et al.
Justus Liebigs Ann. Chem. 388, p. 212 1912 Ullmann et al.
Med Chem. Res. 6:2, 81–101 1996 Castan et al.
Molec. Cell. Biochem. 138:185–97 1994 Banasik et al.
Mutation Research 218, 67–74 1989 Gonzalez et al.
Mutation Research 350, 25–34 1996 Wachsman.
Nature Medicine JHU 1997 Eliasson et al.
Neuron 1, 623–634 1988 Choi.
NeuroReport 5:3, 245–48 1993 Wallis et al.
Nucleic Acids Research 29(3)841–849 2001 Simbulan-Rosenthal et al.
Oncol. Res. 6:9, 399–403 1994 Weltin et al.
Pain vol. 72, pp. 355–366 1997 Mao et al.
Pharm. Bull. 5:289–91 1957 Ochiai et al.
Phosphorus Sulfur vol. 14, No. 1, pp. 131–138 1983 Becher et al.
Proc. Natl. Acad. Sci. USA 88:6368–71 1991 Dawson et al.
Proc. Natl. Acad. Sci. USA 93:1753–58 1996 Szabó et al.
Proc. Natl. Acad. Sci. USA 94:679–83 1997 Thiemermann et al.
Proc. Natl. Acad. Sci. USA vol. 93, pp. 7481–7485 1996 Ruf et al.
Proc. Natl. Acad. Sci. USA 96:5774–5779 (May) 1999 Mandie et al.
Radiat. Res. vol. 116 No. 3, pp. 442–452 1988 Paaphorst et al.
Radiat. Res. 101:29–46 1985 Oleinik.
Res. Comm. Mol. Pathol. Pharmacol. vol. 95 No. 3, pp. 241–252 1997 Lam.
Ric. Sci. 38:3, 231–33 1968 Di Maio et al.
Rocz. Chem. 41:1, 89–101 1967 Schoen et al.
Science 223:589–91 1984 Milam et al.
Science 263:687–89 1994 Zhang et al.
Science 265:1883–1885 1994 Huang et al.
Science 282, 1484–1487 1998 Smith et al.
Shock 5(4):258–64 1996 Zingarelli et al.
Spin Label Analogue of ATP 246, No. 20, 6362–6364 1971 Miwa et al.
Switzerland Patent 601 246 1978.

Terato., Carcino., and Muta. 16:219–27 1996 Cristovao et al.
Tetrahedron supp. 8, part 1, pp. 305–12 1966 Tamayo et al.
Tetrahedron Letters 32, No. 35, 4525–4528 1991 Chida et al.
Tetrahedron Letters 36:33, 5983–86 1995 White et al.
Tetrahedron Letters 52:9, 3117–34 1996 White et al.
The EMBO Journal vol. 16 No. 19, pp. 6018–6033 1997 Vaziri et al.
The Journal of Biological Chemistry 242, No. 22, 5301–5307 1967 Futai et al.
The Journal of Biological Chemistry vol. 257, No. 21, 12872–12877 1982 Wielckens et al.
The Journal of Biological Chemistry 259, No. 2, 986–995 1984 Oka et al.
The Journal of Biological Chemistry 261, No. 2, pp. 965–969 1986 Tanuma et al.
The Journal of Biological Chemistry 263, No. 23, 11037–11040 1988 Ikejima et al.
The Journal of Biological Chemistry 272, No. 18, 11895–11901 1997 Lin et al.
TiPS 11, 379–387 1990 Meldrum et al.
TIPS in press 1998 Pieper et al.
Trends Neurosci. 20:3, 132–139 1997 Iadecola.
Vertex Pharmaceuticals Inc. PR Newswire 1998.

* cited by examiner

METHODS, COMPOUNDS AND COMPOSITIONS FOR TREATING GOUT

This Application claim the benefit from U.S. Provisional Application No. 60/208,328 filed Jun. 1, 2000.

The present invention relates to methods of treating gout with inhibitors of the nuclear enzyme poly(adenosine 5'-diphospho-ribose) polymerase ["poly(ADP-ribose) polymerase" or "PARP", which is also referred to as ADPRT (NAD:protein (ADP-ribosyl transferase (polymersing)) and PARS (poly(ADP-ribose) synthetase) and provides compounds and compositions containing the disclosed compounds for use in the disclosed method.

Reviews of PARP as well as the effects of inhibiting the same may be found, for example, in PCT/US98/18184, PCT/US98/18226, PCT/US98/18187, PCT/US98/18195, PCT/US98/18196, PCT/US98/18188, PCT/US98/18189, PCT/US98/18185, PCT/US98/18186, the entire contents of each of which are hereby incorporated by reference.

Deposition of crystals of monosodium urate (MSU crystals) in the joint articular space is the etiological cause of inflammatory pathologies such as gout and pseudogout. Clinically, these inflammatory diseases are associated with oedema and erythema of the joints with consequently severe pain. A strong infiltration of leucocytes in the intraarticular and periarticular space leading to: 1) acute, episodic articular and periarticular inflammation, and 2) chronic articular changes, are also characteristic of this pathology. It has long been clear that neutrophils are the predominant cell type recovered from these inflammatory joints (Dieppe et al., (1979). Synovial fluid crystals. Q. J. Med. XLVIII: 533–553; Terkletaub, (1991). Monocyte-derived neutrophil chemotactic factor/interleukin-8 is a potential mediator of crystal-induced inflammation. Arth. Rheum. 34: 894–903.). A better understanding of the inflammatory processes elicited by MSU crystals, and the fact that there is a clear relationship between these crystals and gouty arthritis, has prompted the characterisation of experimental models of crystal-induced inflammation. Examples of models where crystal challenge has led to call recruitment into specific cavities, are canine joints (Phelps & McCarty, 1966, Ann Int. Med. 9: 115–125), rat pleurisy (Deporter et al., 1979, Br. J. Pharmacol. 65: 163–165; Sedgwick et al., 1985, Agents Actions 17: 209–213), and utilisation of a pre-formed rat air-pouch (Brookes et al., 1987). The latter experimental system has shown that neutrophil accumulation was related to generation of chemoattractants such as $LTB_4$, which was subsequently inhibited by colchicine (Brooks et al., 1987, Br. J. Pharmacol. 90: 413–419).

Neutrophils have been shown to be activated by MSU crystals, releasing an array of mediators that may be, in part, responsible for the local and systemic inflammatory manifestations found in crystal-induced joint disorders. The crystals interact with neutrophils leading to the release of lysomal enzymes (Hoffstein et al., 1975, Arth. Rheum. 18: 153–165), release of oxygen derived free radicals (Simchowitz et al., 1982, Arth. Rheum. 25: 181–188; Abramson et al., 1982, Arthr Rheum. 25: 174–180), induction of phospholipase $A_2$ ($PLA_2$) in leucocytes (Bomalaski et al., 1990, J. Immunol. 145: 339:–3397), and activation of synthesis of 5-lipoxygenase products (Poubelle et al., 1987, Biochem. Biophys. Res. Commun. 149: 649–657).

In vitro, MSU crystals have been shown to release the cytokine interleukin-1β (IL-1β) from human neutrophils, adding this stimulus to a list of others that also release this cytokine, such as zymosan, LPS, phorbol esters, granulocyte macrophage-colony stimulating hormone (GM-CSF) and TNF-alpha. Furthermore it has also been shown that human monocytes and synoviocytes can synthesise and release various cytokines such as IL-6 and IL-8 (Guerne et al., 1989, Arth. Rheum. 32: 1443–1452; Terkeltaub et al., 1991, Arth. Rheum. 34: 894–903). In addition, colchicine selectively inhibits MSU crystal- and TNF-Z induced release of IL-1β (Roberge et al., 1994, J. Immunol. 152: 5485–5494).

In experimental models of gout the synthesis of a CXC chemokine selective for neutrophils, such as IL-8, has also been observed, but not that of a CC chemokine monocyte chemoattractant protein-1 (MCP-1) (Hachicha et al., 1995, J. Exp. Med. 182: 2019–2025). These results suggest that production of IL-8 and abolition of the release of MCP-1, will lead to an event where, theoretically there will be a recruitment of neutrophils but not mononuclear cells. This hypothesis is in accordance with the pathological state of gout and pseudogout, where the predominant inflammatory cell is the neutrophil (Hachicha et al., 1995). In addition MSU crystal activation of mononuclear phagocytes, which are normally found in the joint space, also induces secretion of IL-8 (Terkeltaub et al., 1991). The importance of IL-8 in this pathology has been shown in synovial fluids of patients with acute gouty arthritis where it occurs in elevated amounts (Terkeltaub et al., 1991; di Giovine et al., 1991, J. Clin. Invest. 87: 1375–1381). The use of a neutralising antibody against IL-8 has been shown significantly to attenuate the crystal induced joint swelling at 12 h and neutrophil infiltration into arthritic joints at 12 and 24 h in a rabbit model (Nishimura et al., 1997, J. Leukoc. Biol. 62: 444–449).

These studies demonstrate the importance of both the emigrating neutrophil and the chemokine IL-8, as well as the release of this and other cytokines from resident cells such as the synoviocytes, macrophages and mast cells in treating gout. Since neutrophils are not present or are extremely rare in normal synovial fluid, enhanced neutrophil-endothelial adhesion is necessary for gout to occur (Terkeltaub, 1996, In. Koopman, W. J. editor. Arthritis and allied conditions: a textbook of rheumatology. Baltimore: Williams and Wilkins: pp. 2085–2102, and Terkeltaub, 1992, In Inflammation. Basic Principles and Clinical Correlates, ed. by J. I. Gallin, I. M. Goldstein and R. Snyderman, pp 977–981, Raven Press, New York). IL-1β and TNF-alpha may be critical in mediating the rapid up-regulation of the major endothelial ligand for neutrophils. For instance rapid and prolonged expression of E-selectin in response to injection of urate crystals has been demonstrated in pig skin (Chapman et al., 1996, Br. J. Rheumatol. 35: 323–334). The release of cytokines, chemokines and products of the arachidonic acid cascade system lead to the recruitment of neutrophils in this pathology, and inhibition of these leads to an attenuation of the pathology.

The following gout model was used to test a PARP inhibitor according to the present invention.

Male outbread Swiss albino mice (20–22 g body weight) were purchased from Banton and Kingsman (T.O. strain; Hull, Humberside) and maintained on a standard chow pellet diet with tap water ad libitum and a 12:00 h light/dark cycle. All animals were housed for 1 week prior to experimentation to allow body weight to reach 28–30 g. 1,11b-dihydrobenzopyrano[4,3,2-de ]isoquinolin-1-one was dissolved in 100% DMSO at room temperature at a concentration of 45 mg in 2 ml. The compound was then injected into the peritoneal cavity, so as each mouse received a single dose corresponding to 45 mg/2 ml/kg (e.g. 60 μl for a mouse of 30 g). Control mice received DMSO at 2 ml/kg i.p. A third group of mice which were left untreated were added to control for potential effects of the vehicle. The study involved therefore, the following three groups: group A, untreated mice, n=6, group B, DMSO-treated mice, n=8, and group C, mice treated with 1,11b-dihydrobenzopyrano[4,3,2-de]isoquinolin-1-one, n=8

MSU crystal-induced neutrophil recruitment was tested as follows. In all cases, mice were treated 1 h after the treatment noted above, with MSU crystals. A homogenous suspension of MSU crystals was obtained by a 30 min rotation. Peritonitis was induced by injection of 3 mg MSU crystals in 0.5 ml PBS (0.1 M, pH 7.4), and the recruitment of neutrophils into the cavity evaluated at the 6 h time point (Getting et al., 1997, *J. Pharmacol. Exp. Ther.* 2.33: 123–130). Animals were then euthanised by $CO_2$ exposure and the peritoneal cavity washed with 3 ml of PBS supplemented with 3 mM EDTA and 25 U/ml heparin.

An aliquot (100 μl) of the lavage fluid was then diluted 1:10 in Turk's solution (0.01% crystal violet in 3% acetic acid). The samples were then vortexed and 10 μl of the stained cell solution were placed in a Neubauer haematocymometer and neutrophils numbers counted using a light microscope (Olympus B061). Cell-free supernatants have been prepared by centrifugation and stored for potential future analysis.

Data are shown for single mice, and also shown as mean±S.E. of (n) mice per group. Statistical differences were determined by ANOVA, plus Bonferrconi test. A P value <0.05 was taken as significant.

TABLE I reports the number of neutrophils as measured 6 h post-MSU crystal injection in the three experimental groups.

TABLE I

Effect of 1,11b-dihydrobenzopyrano[4,3,2-de]isoquinolin-1-one on MSU crystal induced neutrophil migration as evaluated at the 6 h time-point.

| Mouse No. | Group | Neutrophil Numbers | Group | Neutrophil Numbers | Group | Neutrophil Numbers |
|---|---|---|---|---|---|---|
| 1 | A | 4.9 | B | 6.0 | C | 5.1 |
| 2 | A | 5.4 | B | 6.6 | C | 2.1 |
| 3 | A | 6.3 | B | 7.5 | C | 2.4 |
| 4 | A | 6.9 | B | 7.8 | C | 2.4 |
| 5 | A | 5.7 | B | 5.1 | C | 3.0 |
| 6 | A | 6.0 | B | 5.7 | C | 3.0 |
| 7 | | | B | 5.7 | C | 2.7 |
| 8 | | | B | 6.0 | C | 2.1 |

Legend: Mice were left untreated (group A), received vehicle DMSO (2 ml/kg i.p.; group B) or 1,11b-dihydrobenzopyrano[4,3,2-de]isoquinolin-1-one (45 mg/kg i.p.; group C), 1 h prior to peritoneal injection of 3 mg MSU crystals at time 0. Neutrophil influx in the peritoneal cavity was measured at the 6 h time-point after collection of the lavage fluids and specific staining as described in the experimental section. Values for neutrophil numbers are $10^6$ per mouse.

TABLE II illustrates these data as mean±S.E. It can be seen that DMSO produced a modest not significant increase in cell migration (+7%). In contrast, the exemplary compound of the present invention, at the dose of 45 mg/kg, significantly reduced cell influx, with a calculated 55% of inhibition vs. the vehicle group.

TABLE II

Accumulation of data for the effect of the exemplified compound of the present invention (means).

| Experimental Group | Stimulus | Neutrophils ($10^6$ per mouse) |
|---|---|---|
| A | MSU crystals (3 mg) | 5.87 ± 0.28 (6) |
| B | MSU crystals (3 mg) | 6.30 ± 0.33 (8) |
| C | MSU crystals (3 mg) | 2.85 ± 0.34 (8)* |

Legend: as in TABLE II.
Values are mean ± S.E. of (n) mice per group.
*$P < 0.05$ vs. group B.

The above results demonstrate the ability of a PARP inhibitor to prevent neutrophil recruitment in response to MSU crystal-induced, or urate crystal-induced, activation, within the present invention.

The present invention therefore, provides a method of preventing, treating and/or lessening the severity of leukocyte, specifically neutrophil, recruitment in response to urate crystals and, more generally, provides a method of preventing, treating and/or lessening the severity of gout.

Compounds useful in the present invention include PARP inhibitors disclosed and methods of making the same in any of PCT/U.S. Ser. No. 98/18184, PCT/U.S. Ser. No. 98/18226, PCT/U.S. Ser. No. 98/18187, PCT/U.S. Ser. No. 98/18195, PCT/U.S. Ser. No. 98/18196, PCT/U.S. Ser. No. 98/18188, PCT/U.S. Ser. No. 98/18189, PCT/U.S. Ser. No. 98/18185, PCT/U.S. Ser. No. 98/18186, and U.S. application Ser. Nos. 08/922520, 09/079513, 09/145179, 09/079508, 09/145166, 09/079507, 09/145177, 09/145180, 09/079509, 09/079510, 09/145184, 09/079511, 09/145185, 08/922548, 09/145181, 09/147502, 09/219843, 08/922575, 09/079512, 09/145176, 09/079514, 09/145178, 09/224293, 09/224294 and 09/387767, the entire contents of each of which are hereby incorporated by reference.

Further PARP inhibitor compounds which will be useful in the methods of the present invention include compounds of the following general formula shown below and derivatives thereof, with specific exemplary compounds (the entire contents of each noted reference is hereby incorporated by reference for specific compounds and methods of making the same):

Benzamide and substituted benzamide (as described, for example, in U.S. Pat. No. 5,587,384)

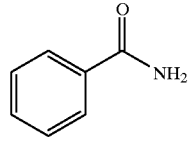

specific examples include:

3-aminobenzamide, and 3-hydroxybenzamide.

Benzoxazole-4-carboxamide (as described, for example, in EP 0879820)

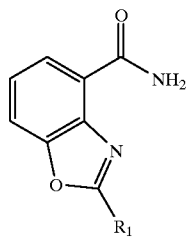

specific examples include:
2-phenylbenzoxazole-4-carboxamide (NU1051),
2-(4-methoxyphenyl) benzoxazole-4-carboxamide (NU1054), and
2-methylbenzoxazole-4-carboxamide (NU1056).

Quinazolin-4-[3H] one (as described, for example, in EP 0897915)

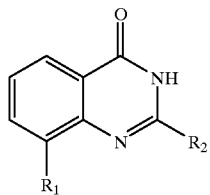

specific examples include:
8-methoxy-2-methylquinazolin-4-[3H]one,
8-methoxy-2-phenylquinazolin-4-[3H]one,
8-hydroxy-2-phenylquinazolin-4-[3H]one, and
2,8-dimethylquinazolin-4-[3H]one.

3,4-Dihydro-1(2H)-isoquinolinone and 1(2H)-isoquinolinone (as described, for example, in U.S. Pat. No. 5,177,075)

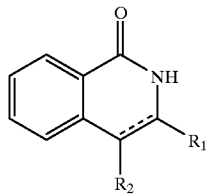

specific examples include:
3,4-Dihydro-5-nitro-1(2H)-isoquinolinone,
3,4-Dihydro-7-nitro-1(2H)-isoquinolinone,
5-Amino-3,4-dihydro-1(2H)-isoquinolinone,
7-Amino-3,4-dihydro-1(2H)-isoquinolinone,
3,4-Dihydiro-1(2H)-isoquinolinone,
3,4-Dihydro-5-[2-hydroxy-3-(1piperidinyl)propoxy]-1(2H)-isoquinolinone,
5-(Acetyloxy)-3,4-dihydro-1(2H)-isoquinolinone and
3,4-Dihydro-5-(phenylmethoxy)-1(2H)-isoquinolinone.

1,6-Naphthyridine-5(6H)-one(as described, for example, in U.S. Pat. No. 5,391,554)

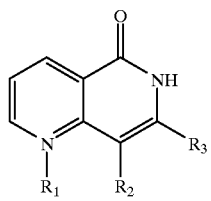

specific examples include:
7-Methyl-1,6-Naphthyridine-5(6H)-one and
7,8-Dihydro-1,6-Naphthyridine-5(6H)-one.

6(5H)phenanthridinone (as described in the above-identified applications)

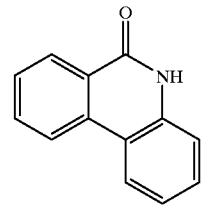

specific examples include:
2-amino-10-hydroxy-6(5H)phenanthridinone and those shown below.

8-Carbainoylnaphthalenecarboxylic acid derivatives (as described in the above-identified applications) and specific examples provided below.

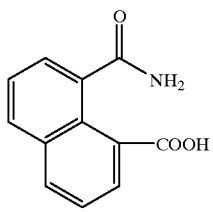

Specific examples of these derivatives include the following:

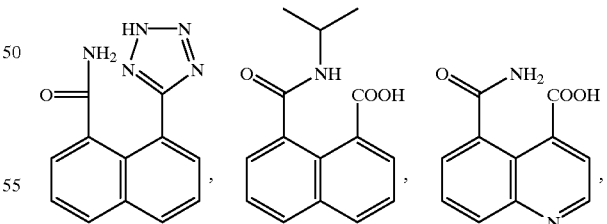

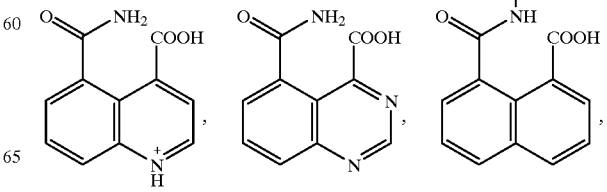

-continued
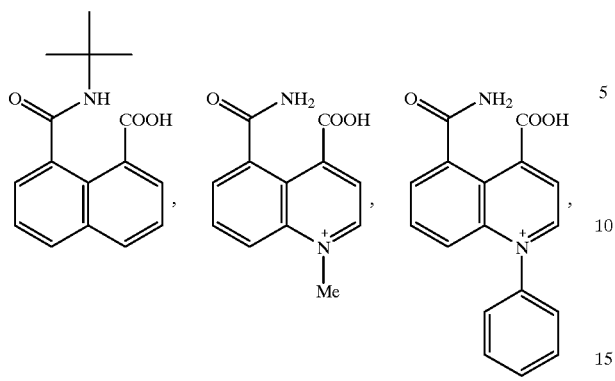
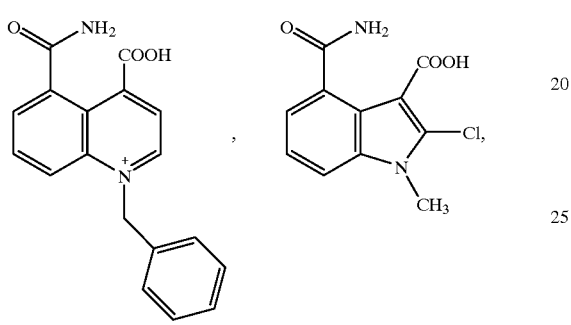
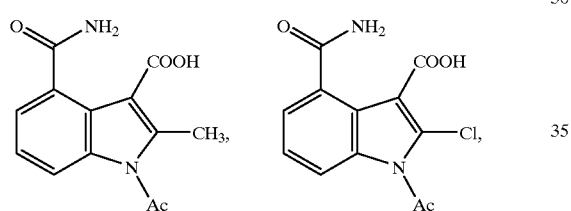
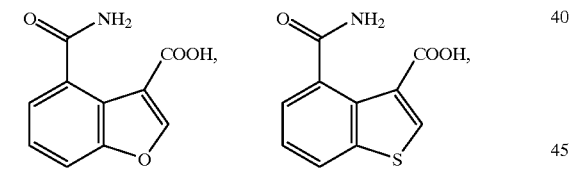
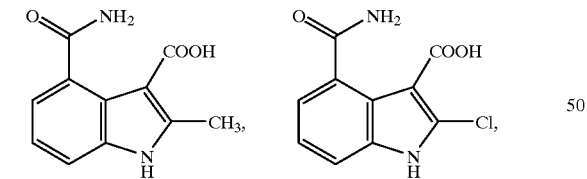
and
[de]-fused isoquinolin-1-one (as described in the above-identified applications) and specific examples provided below
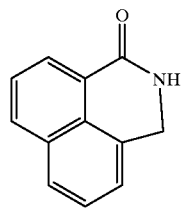
The following are specific examples of these derivatives:
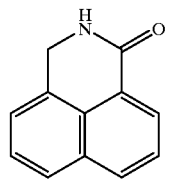
I
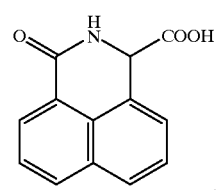
II
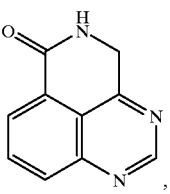
III
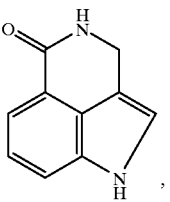
IV
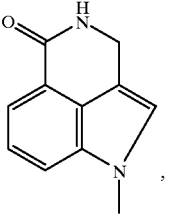
V
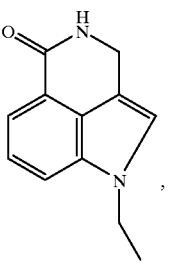
VI Lactam fused xanthene (as described in the above-identified applications) and specific examples provided below (wherein, for example Y may be CH, CH₂ or N)

Substituted xanthene lactam (as described in the above-identified applications) and specific examples provided below -continued
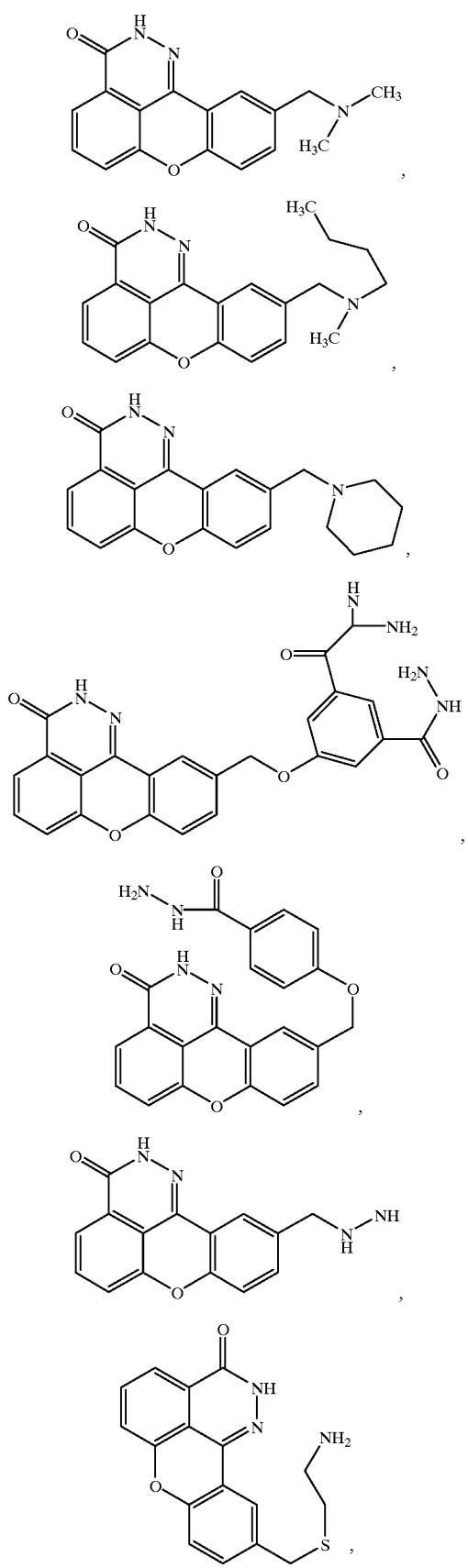
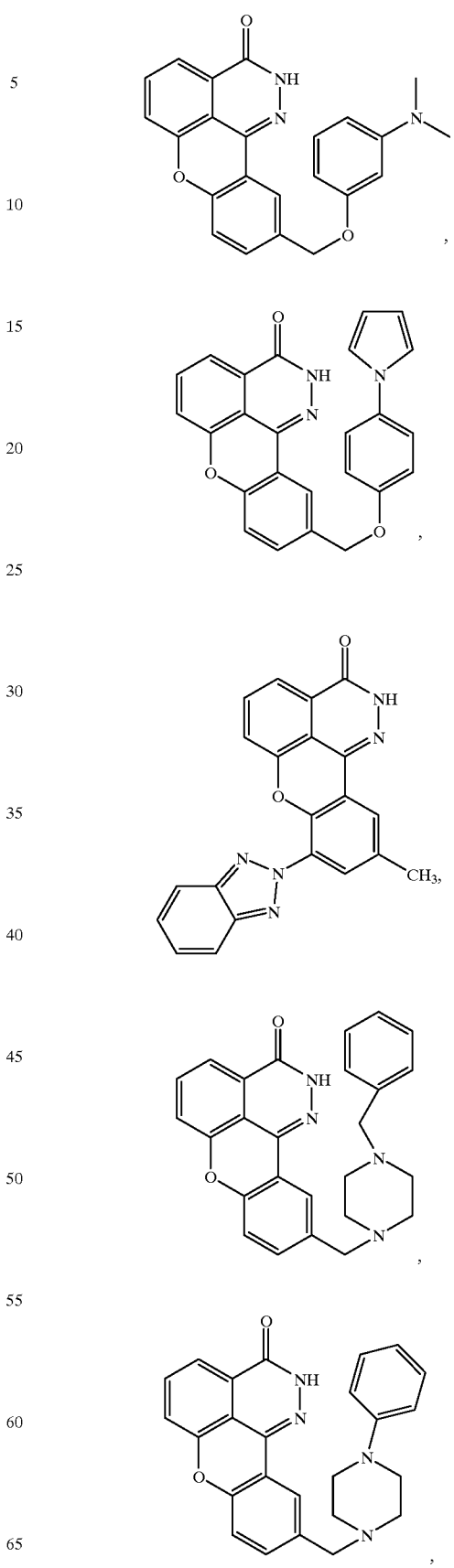

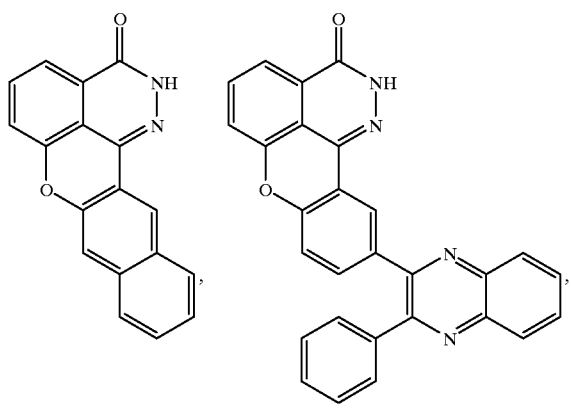
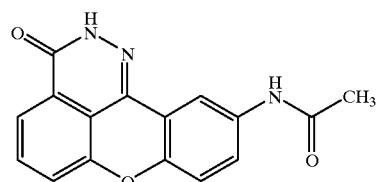
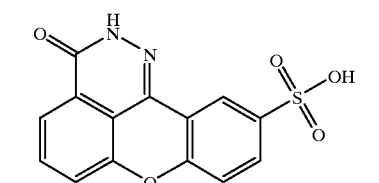
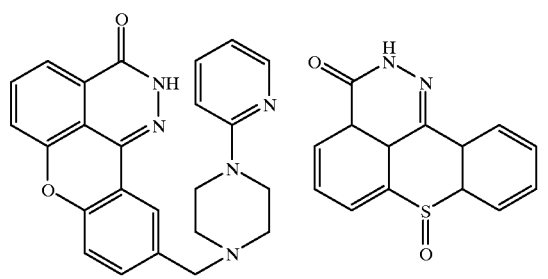
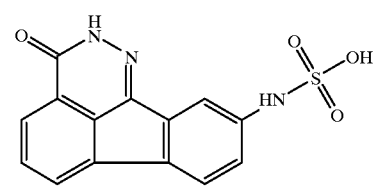
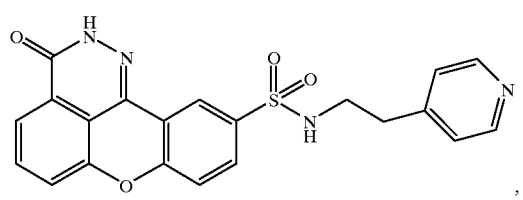
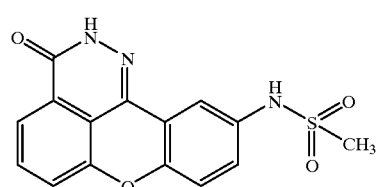
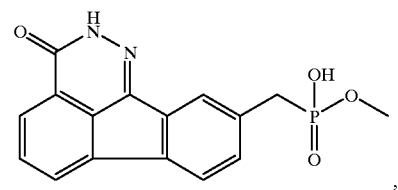
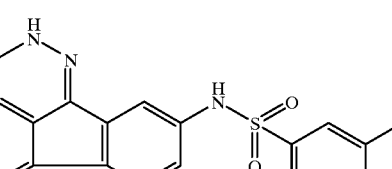
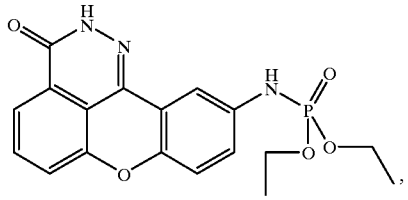
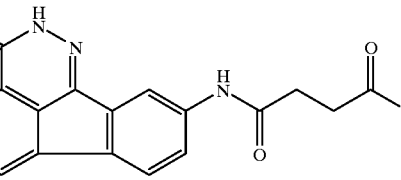
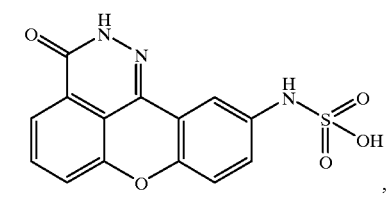
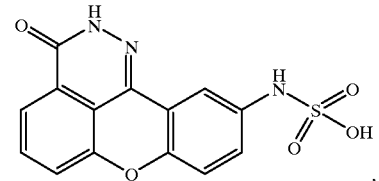
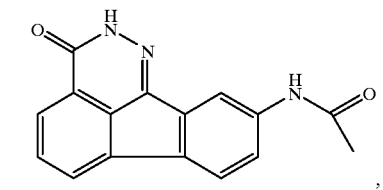
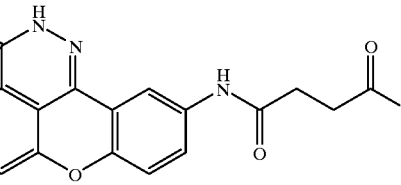

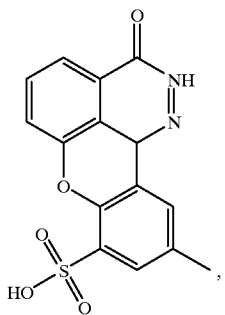
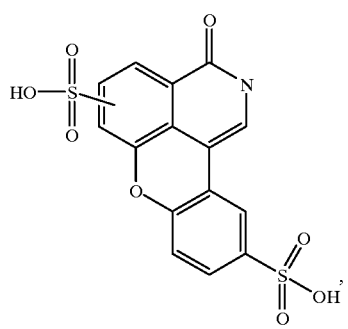
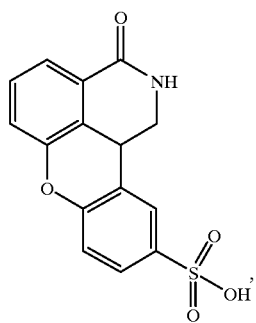
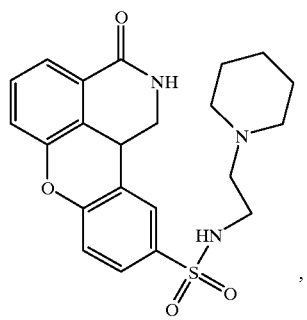
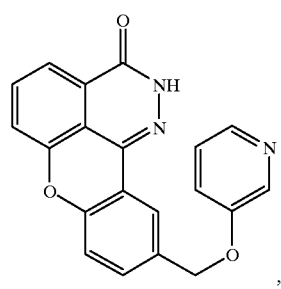
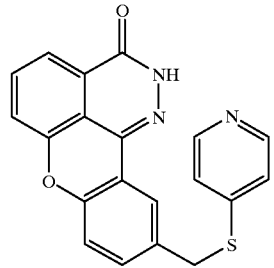
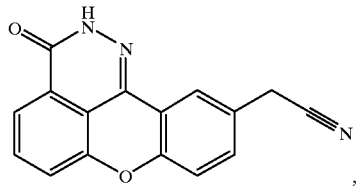
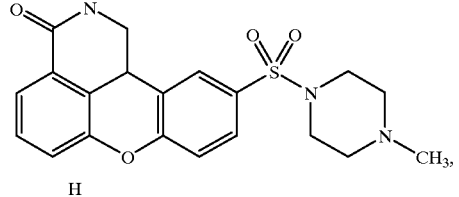
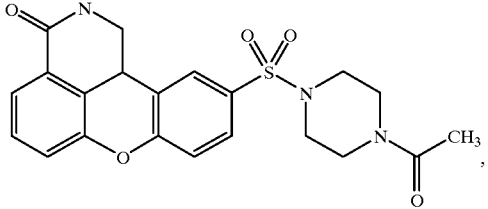
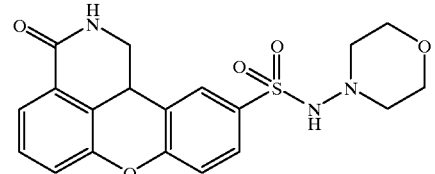
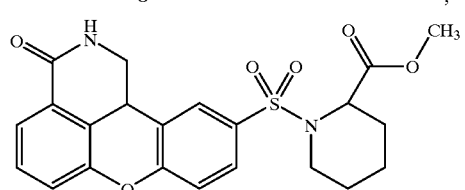
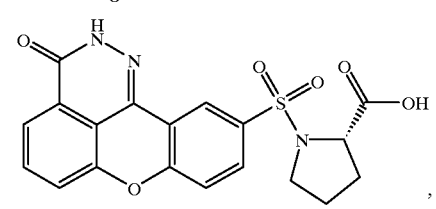
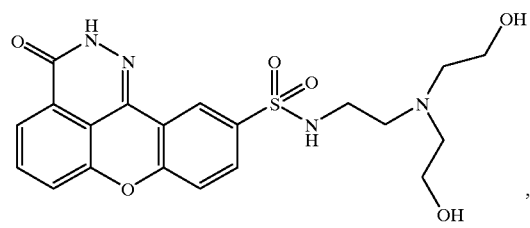

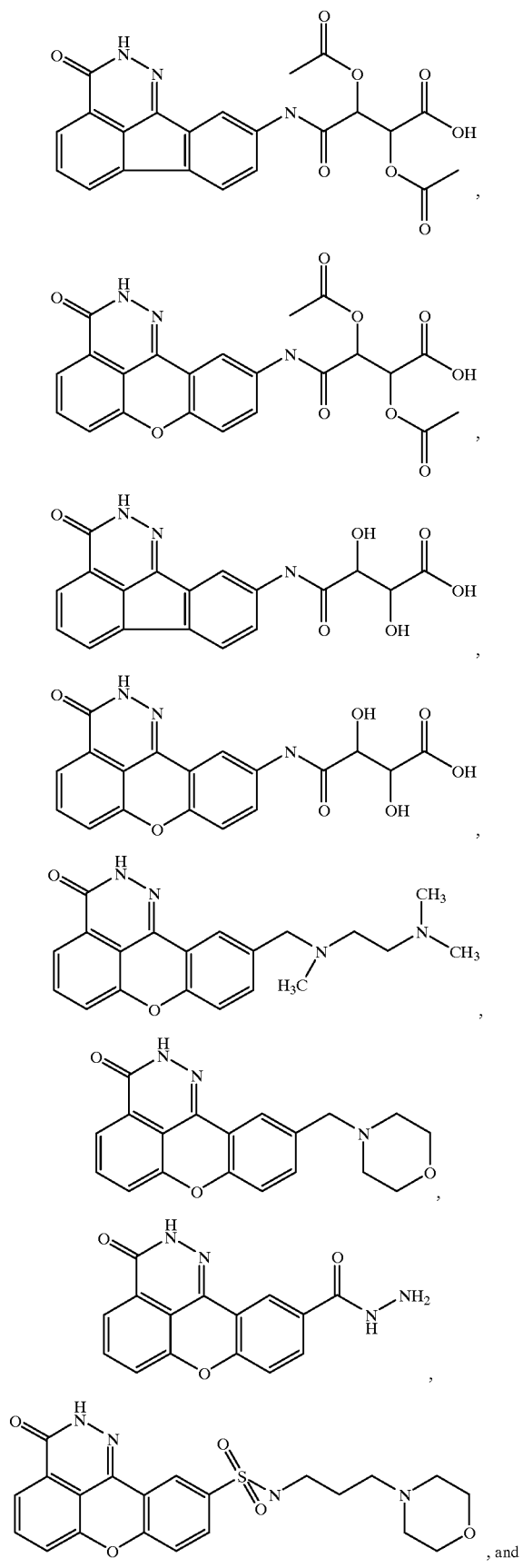

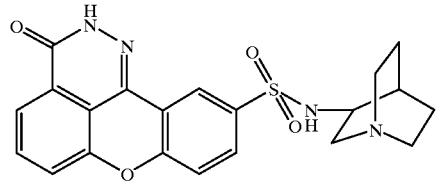

Further specific examples of useful inhibitors include:
N-(1,2, 3,4-tetrahydro-1-oxo-5-isoquinolinyl)acetamide,
1-hydroxyisoquinoline,
5-amino-3,4-dihydro-1(2H)-isoquinolinone and its monohydrochloride salt,
3,4-dihydro-5-[(1-phenylmethyl)-amino]-1(2H)-isoquinolinone,
3,4-dihydro-5-methyl-1(2H)-isoquinolinone,
5-ethyl-3,4-dihydro-1(2H)-isoquinolinone,
5-ethoxy-3,4-dihydro-1(2H)-isoquinolinone,
5-chloro-3,4-dihydro-1(2H)-isoquinolinone,
4-bromo-5-methyl-1(2H)-isoquinolinone,
4-bromo-5-hydroxy-1(2H)-isoquinolinone,
3,4-dihydro-5-methoxy-1(methylthio)isoquinolinone,
3,4-dihydro-5-propoxy-1(2H)isoquinolinone,
3,4-dihydro-5-butoxy-1(2H)isoquinolinone,
3,4-dihydro-5-(2-hydroxy-3-methoxypropoxy-1(2H) isoquinolinone,
3,4-dihydro-5-(2-hydroxy-3-phenoxypropoxy-1(2H) isoquinolinone,
3,4-dihydro-5-(2-hydroxy-3-phenylpropoxy-1(2H) isoquinolinone,
3,4-dihydro-5-(phenylethoxy-1(2H)isoquinolinone,
3,4-dihydro-3,5-dimethyl-1(2H)-isoquinolinone,
3,4-dihydro-5-methyl-1-(methylthio)isoquinolinone,
3,4-dihydro-5-(dimethylamino)-1(2H)-isoquinolinone and its hydrochloride salt,
3,4-dihydro-5-[3-(1-piperidinyl)propoxy]-1(2H)-isoquinolinone,
3,4-dihydro-5-[2-(1-piperidinyl)ethoxy]-1(2H)-isoquinolinone,
3,4-dihydro-5-[4-(1-piperidinyl)-butoxy]-1(2H)-isoquinolinone,
1,8-naphthalimide,
4-amino-1,8-naphthalimide,
6(5H)-phenanthridinone,
2-nitro-6(5H)-phenanthridinone,
1(2H)-phthalazinone,
5-methoxy-4-methyl-1(2H)-phthalazinone,
phthalhydrazide (1,4-dioxo-1,2,3,4-tetrahydrophthalazine, also known as 2,3-dihydro-1,4-phthalazinedione),
4-hydroxyquinazoline,
phthalazinedione,
5-amino-2,3-dihydro-1,4-phthalazinedione (luminol),
4-hydroxyquinazoline,
2-methyl-4(3H)-quinazolinone,
2-mercapto-4(3H)-quinazolinone,
2,4(1H,3H)-quinazolinedione,
1,11b-dihydrobenzopyrano[4,3,2-de ]isoquinolin-1-one,
N-hydroxynaphthalimide sodium salt, and
the pharmacologically acceptable base or acid addition salts thereof.

Other compounds useful in the present invention include compounds of the following formula:

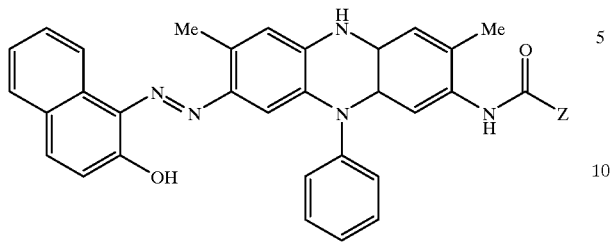

wherein Z is any of the following:

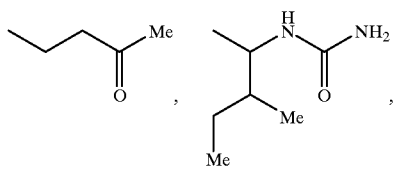

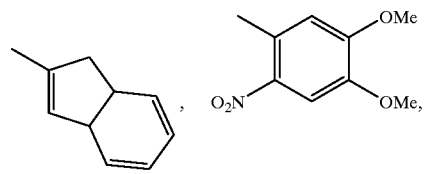

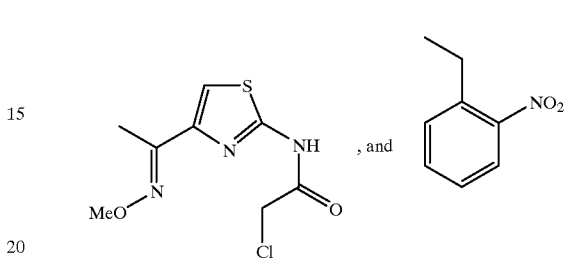

Further compounds useful in the present invention include the following, with reference to the following structure:

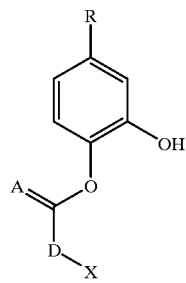

| R | A | D | x |
|---|---|---|---|
| methyl | O | bond | 4-bromophenyl |
| ethyl | O | bond | phenyl |
| n-propyl | O | bond | 3,4,5-trihydroxy-phenyl |
| i-propyl | O | bond | 3,4,5-trimethoxy-phenyl |
| n-butyl | O | bond | 3-hydroxyphenyl |
| t-butyl | O | bond | 4-nitro-naphthyl |
| s-butyl | O | bond | 3-hydroxy-naphthyl |
| pentyl | O | bond | benzyl |
| hexyl | O | bond | 4-ethylphenyl |
| heptyl | O | bond | 4-ethenylphenyl |
| octyl | O | bond | 4-quinolyl |
| nonyl | O | bond | 2-thiazolyl |
| decyl | O | bond | 3-furyl |
| 1,1-dimethylpropyl | O | bond | phenyl |
| ethenyl | O | bond | cyclohexyl |
| prop-2-enyl | O | bond | 3-bromocyclohexyl |
| phenyl | O | bond | adamantyl |
| naphthyl | O | bond | 4-indolyl |
| 4-nitrophenyl | O | bond | 2-imidazolyl |
| 4-hydroxyphenyl | O | bond | 1-naphthyl |
| 4-chlorophenyl | O | bond | 4-nitrophenyl |
| 4-methylphenyl | O | bond | 4-hydroxyphenyl |
| 4-methoxyphenyl | O | bond | 3-piperidyl |
| 4-dimethylamino-phenyl | O | bond | 3,4,5-trimethyl-phenyl |
| phenyl-ethyl-phenyl | O | bond | 3-pyridyl |
| 4-nitro-3-hydroxy-phenyl | O | bond | 3,4,5-trifluoro-phenyl |
| 1-pyridyl | O | bond | 1-pyrrolidyl |
| 1-piperidyl | O | bond | 4-phenylazo-phenyl |

-continued

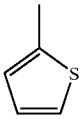

| R | A | D | x |
|---|---|---|---|
| 1-pyrrolidyl | O | 2-bromo-propyl | 4-amino-3-hydroxy-phenyl |
| cyclohexyl | O | prop-2-enyl | 3,4,5-triamino-phenyl |
| cyclopentyl | O | methyl | 4-hydroxyphenyl |
| adamantyl | O | ethyl | phenyl |
| benzyl | O | i-propyl | 9-anthracenyl |
| 4-hydroxybenzyl | O | n-propyl | 4-pyrenyl |
| 3,4,5-trihydroxy-phenyl | O | 2-imino-propyl | 3-furyl |
| thiazolyl | O | 2-thio-propyl | 3-thiophenyl |
| 2-phenylethyl | O | 2-sulfonyl-propyl | 4-pyrimidinyl |
| 3-phenylpropyl | O | ethenyl | 4-isoquinolyl |
| 2-phenylethenyl | O | bond | 4-sulfonylphenyl |
| 3-phenylprop-2-enyl | O | chloro-methyl | 4-imino-phenyl |
| 3-bromopropyl | O | —CH$_2$—N=CH— | 4-phenylethoxy-phenyl |
| 4-fluoro-n-butyl | O | —CH$_2$—S—CH$_2$— | 4-ethylphenoxy-phenyl |
| 3-methoxypropyl | O | —CH$_2$—NH—CH$_2$— | 4-phenoxy-phenyl |
| 2-hydroxyethyl | O | —CH$_2$—O—CH$_2$— | 3-phenylpropyl-phenyl |
| tert-butyl | O | —CH$_2$— | 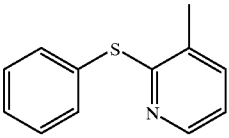 |
| tert-butyl | O | bond | 2-chloro-phenyl |
| tert-butyl | O | bond | 4-chloro-phenyl |
| tert-butyl | O | bond | 3,4,5-trimethoxy-phenyl |
| tert-butyl | O | bond | 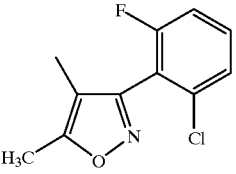 |
| tert-butyl | O | bond | |
| tert-butyl | O | —O—CH$_2$—, X attaches directly to the CH$_2$ | phenyl |
| methyl | S | bond | 4-bromophenyl |
| ethyl | S | bond | phenyl |
| n-propyl | S | bond | 3,4,5-trihydroxy-phenyl |
| i-propyl | S | bond | 3,4,5-trimethoxy-phenyl |
| n-butyl | S | bond | 3-hydroxyphenyl |
| t-butyl | S | bond | 4-nitro-naphthyl |

-continued

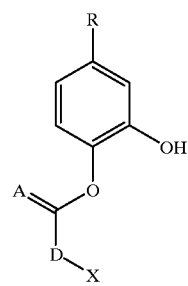

| R | A | D | x |
|---|---|---|---|
| s-butyl | S | bond | 3-hydroxy-naphthyl |
| pentyl | S | bond | benzyl |
| hexyl | S | bond | 4-ethylphenyl |
| heptyl | S | bond | 4-ethenylphenyl |
| octyl | S | bond | 4-quinolyl |
| nonyl | S | bond | 2-thiazolyl |
| decyl | S | bond | 3-furyl |
| 1,1,dimethylpropyl | S | bond | phenyl |
| ethenyl | S | bond | cyclohexyl |
| prop-2-enyl | S | bond | 3-bromocyclohexyl |
| phenyl | S | bond | adamantyl |
| naphthyl | S | bond | 4-indolyl |
| 4-nitrophenyl | S | bond | 2-imidazolyl |
| 4-hydroxyphenyl | S | bond | 1-naphthyl |
| 4-chlorophenyl | S | bond | 4-nitrophenyl |
| 4-methylphenyl | S | bond | 4-hydroxyphenyl |
| 4-methoxyphenyl | S | bond | 3-piperidyl |
| 4-dimethylamino-phenyl | S | bond | 3,4,5-trimethyl-phenyl |
| phenyl-ethyl-phenyl | S | bond | 3-pyridyl |
| 4-nitro-3-hydroxy-phenyl | S | bond | 3,4,5-trifluoro-phenyl |
| 1-pyridyl | S | bond | 1-pyrroildyl |
| 1-piperidyl | S | bond | 4-phenylazo-phenyl |
| 1-pyrrolidyl | S | 2-bromo-propyl | 4-amino-3-hydroxy-phenyl |
| cyclohexyl | S | prop-2-enyl | 3,4,5-triamino-phenyl |
| cyclopentyl | S | methyl | 4-hydroxyphenyl |
| adamantyl | S | ethyl | phenyl |
| benzyl | S | i-propyl | 9-anthracenyl |
| 4-hydroxybenzyl | S | n-propyl | 4-pyrenyl |
| 3,4,5-trihydroxy-phenyl | S | 2-imino-propyl | 3-furyl |
| thiazolyl | S | 2-thio-propyl | 3-thiophenyl |
| 2-phenylethyl | S | 2-sulfonyl-propyl | 4-pyrimidinyl |
| 3-phenylpropyl | S | ethenyl | 4-isoquinolyl |
| 2-phenylethenyl | S | bond | 4-sulfonylphenyl |
| 3-phenylprop-2-enyl | S | chloro-methyl | 4-imino-phenyl |
| 3-bromopropyl | S | —CH$_2$—N=CH— | 4-phenylethoxy-phenyl |
| 4-fluoro-n-butyl | S | —CH$_2$—S—CH$_2$— | 4-ethylphenoxy-phenyl |
| 3-methoxypropyl | S | —CH$_2$—NH—CH$_2$— | 4-phenoxy-phenyl |
| 2-hydroxyethyl | S | —CH$_2$—O—CH$_2$— | 3-phenylpropyl-phenyl |
| tert-butyl | S | —CH$_2$— | |
| tert-butyl | S | bond | 2-chloro-phenyl |
| tert-butyl | S | bond | 4-chloro-phenyl |
| tert-butyl | S | bond | 3,4,5-trimethoxy-phenyl |

-continued

| R | A | D | x |
|---|---|---|---|
| tert-butyl | S | bond | (3-methyl-2-(phenylthio)pyridine) |
| tert-butyl | S | bond | (3-(2-chloro-6-fluorophenyl)-4-methylisoxazol-5-yl) |
| tert-butyl | S | —O—CH$_2$—, X attaches directly to the CH$_2$ | phenyl |

Also included as useful compounds in the present methods are the pharmaceutically acceptable salts, hydrates, esters, solvates, prodrugs, metabolites, and stereoisomers of the compounds and derivatives described herein.

The methods of the present invention may be administered to a mammal, such as a human, locally and/or systemically. The compounds of the present invention may be administered, for example, parenterally, either by intermittent or continuous intravenous administration, by either a single dose or a series of divided doses. Compounds of the invention may be used in combination or sequentially. The compound of the invention can be administered by intermittent or continuous administration via implantation of a biocompatible, biodegradable polymeric matrix delivery system containing a compound described herein, or via a subdural pump inserted to administer the compound directly to the site of gout symptoms. Alternatively, a compound of the present invention may be administered topically, through a patch or other transdermal delivery system to the site of gout symptoms.

Preferably, the compounds of the invention exhibit an IC$_{50}$ for inhibiting PARP in vitro, as measured by the methods described herein, of about 20 μM or less, preferably less than about 10 μM, more preferably less than about 1 μM, or less than 0.1 μM, most preferably less than about 0.01 μM.

The compounds of the invention are useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methylglucamine; L-glutamine; N-methylpiperazine; morpholine; ethylenediamine; N-benzyl-phenethylamine; (trihydroxymethyl)aminoethane; and the like. See, for example, "Pharmaceutical Salts," J. Pharm. Sci., 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diaryl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor of the present invention in an aqueous or an aqueous alcohol solution or other suitable solvent containing the appropriate acid or base, and isolating the salt by evaporating the solution. Alternatively, the free base of the PARP inhibitor of the present invention can be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172–178, 949–982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since most drugs undergo metabolic transformation of some kind, the biochemical reactions that play a role in drug metabolism may be numerous and diverse. The main site of drug metabolism is the liver, although other tissues may also participate.

The term "treating" refers to:
(i) preventing a disease, disorder or condition from occurring in an animal that may be predisposed to the disease, disorder and/or condition, but has rot yet been diagnosed as having it;
(ii) inhibiting the disease, disorder or condition, i.e., arresting its development; and
(iii) relieving the disease, disorder or condition, i.e., causing regression of the disease, disorder and/or condition.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are each transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

Phase I Reactions (functionalization reactions):

(1) Oxidation via the hepatic microsomal P450 system:

Aliphatic oxidation
    Aromatic hydroxylation
    N-Dealkylation
    O-Dealkylation
    S-Dealkylation
    Epoxidation
    Oxidative deamination
    Sulfoxide formation
    Desulfuration
    N-Oxidation amd N-hydroxylation
    Dehalogenation (2) Oxidation via nonmicrosomal mechanisms:

Alcohol and aldehyde oxidation
    Oxidative deamination (monoamine oxidase and diamine oxidase)

(3) Reduction:

Azo and nitro reduction (4) Hydrolysis:

Ester and amide hydrolysis
    Peptide bond hydrolysis
    Epoxide hydration

TABLE II-continued

Phase II Reactions (conjugation reactions):

(1) Glucuronidation
(2) Acetylation
(3) Mercapturic acid formation
(4) Sulfate conjugation
(5) N-, O-, and S-methylation
(6) Trans-sulfuration The compounds of the present invention exhibit pharmacological activity and are, therefore, useful as pharmaceuticals. In particular, the compounds exhibit central nervous and cardiac vesicular system activity. It is understood that tautomeric forms, when possible, are included in the invention.

Many of the PARP inhibitors are known and, thus, can be synthesized by known methods from starting materials that are known, may be available commercially, or may be prepared by methods used to prepare corresponding compounds in the literature. See, for example, Suto et al., "Dihydroisoquinolincnes: The Design and Synthesis of a New Series of Potent Inhibitors of Poly(;SP-ribose) Polymerase", Anticancer Drug Des., 6:107–17 (1991), which discloses processes for synthesizing a number of different PARP inhibitors. Further processes for synthesizing compounds useful in the methods of the present invention are described in the above-noted international and U.S. patent applications.

Typically, the PARP inhibitors used in the composition of the invention will have an $IC_{50}$ for inhibiting poly(ADP-ribose) polymerase in vitro of about 20 $\mu$M or less, preferably less than about 10 $\mu$M, more preferably less than about 1 $\mu$M, or preferably less than about 0.1 $\mu$M, most preferably less than about 0.01 $\mu$M.

The compounds of the present invention may be useful in the free base form, in the form of base salts where possible, and in the form of addition salts, as well as in the free acid form. All these forms are within the scope of this invention. In practice, use of the salt form amounts to use of the base form. Pharmaceutically acceptable salts within the scope of this invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like respectively, or those derived from bases such as suitable organic and inorganic bases. Examples of pharmaceutically acceptable base addition salts with compounds of the present invention include organic bases which are nontoxic and strong enough to form such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methylgiucamine; L-glutamine; N-methylpiperazine; morpholine; ethylenedianane; N-benzylphenethylamine; tris (hydroxymethyl) antinoethane; and the like.

The acid addition salts of the basic compounds may he prepared by dissolving the free base of the compounds of the present invention in aqueous or aqueous alcohol solution or other suitable solvents containing the appropriate acid or base and isolating the salt by evaporating the solution, or by reacting the free base of a compound of the present invention with an acid as well as reacting a compound of the present invention having an acid group thereon with a base such that the reactions are in an organic solvent, in which case the salt separates directly or can be obtained by concentration of the solution.

The compounds of this invention contain one or more asymmetric carbon atoms. Therefore, the invention includes the individual stereoisomers and mixtures thereof as well as the racemic compounds. The individual isomers may be prepared or isolated by methods known in the art.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic: parenterally-acceptable diluents or solvents, for example, as solutions in 1,3-butanediol. Among the acceptable vehicles and solvents that may be employed are water, saline, Ringer's solution, dextrose solution isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. The compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. The compositions are prepared according to conventional mixing, granulating, or coating methods, and contain about 0.1 to 75% by weight, preferably about 1 to 50% by weight, of the active ingredient.

Doses of the compounds preferably include pharmaceutical dosage units comprising an efficacious quantity of active compound. By an efficacious quantity is meant a quantity sufficient to inhibit PARP and derive its beneficial effects through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The invention being thus described, it will be obvious that the same may be varied in many ways. Such variations are not to be regarded as a departure from the spirit and scope of the invention, and all such modifications are intended to be included within the scope of the following claims. All references cited herein are incorporated in their entirety by reference herein.

What is claimed is:

1. A method for treating gout in an animal comprising the step of administering an effective amount of a PARP inhibitor compound to said animal.

2. The method of claim 1 wherein said animal is a mammal.

3. The method of claim 1 wherein said animal is a human.

4. A method of preventing urate crystal-induced neutrophil recruitment in a mammal comprising administering a PARP inhibitor to said mammal.

* * * * *